United States Patent
Haider et al.

(10) Patent No.: US 7,508,204 B2
(45) Date of Patent: Mar. 24, 2009

(54) METHOD FOR SUPPORTING AN MRI EXAMINATION BY MEANS OF POSITIONING AND CHECKING MRI ACCESSORY IMPLEMENTATION

(75) Inventors: Sultan Haider, Erlangen (DE); Peter Kreisler, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/385,579

(22) Filed: Mar. 21, 2006

(65) Prior Publication Data

US 2006/0235291 A1 Oct. 19, 2006

(30) Foreign Application Priority Data

Mar. 24, 2005 (DE) .................. 10 2005 013 851

(51) Int. Cl.
*G01V 3/00* (2006.01)
*A06B 5/055* (2006.01)

(52) U.S. Cl. ............. 324/307; 324/309; 324/318; 324/322; 600/414; 600/426; 600/411; 600/410

(58) Field of Classification Search ......... 324/300–322; 600/407–429
See application file for complete search history.

(56) References Cited

U.S. PATENT DOCUMENTS

| | | | | |
|---|---|---|---|---|
| 5,676,673 A * | 10/1997 | Ferre et al. | .................. | 606/130 |
| 6,129,668 A * | 10/2000 | Haynor et al. | ............. | 600/424 |
| 6,263,230 B1 * | 7/2001 | Haynor et al. | ............. | 600/424 |
| 6,405,072 B1 * | 6/2002 | Cosman | ..................... | 600/426 |
| 6,470,207 B1 * | 10/2002 | Simon et al. | ................ | 600/426 |
| 6,534,982 B1 * | 3/2003 | Jakab | ........................ | 324/318 |
| 6,640,597 B2 * | 11/2003 | Beeck et al. | .................. | 72/112 |
| 6,661,227 B2 | 12/2003 | Eggers et al. | | |
| 6,662,036 B2 * | 12/2003 | Cosman | ..................... | 600/411 |
| 6,879,160 B2 * | 4/2005 | Jakab | ........................ | 324/318 |
| 6,961,608 B2 * | 11/2005 | Hoshino et al. | ............ | 600/423 |
| 7,081,748 B2 * | 7/2006 | Jakab | ........................ | 324/302 |
| 2002/0058868 A1 * | 5/2002 | Hoshino et al. | ............ | 600/423 |
| 2002/0124615 A1 * | 9/2002 | Beeck et al. | .................. | 72/112 |
| 2003/0092980 A1 | 5/2003 | Nitz | | |
| 2006/0058633 A1 * | 3/2006 | Hoshino et al. | ............ | 600/410 |
| 2006/0235291 A1 * | 10/2006 | Haider et al. | ............... | 600/415 |

FOREIGN PATENT DOCUMENTS

| | | |
|---|---|---|
| DE | 101 56 215 A1 | 6/2003 |
| EP | 0 487 201 A1 | 5/1992 |
| EP | 1 271 172 A2 | 1/2003 |

* cited by examiner

*Primary Examiner*—Brij B Shrivastav
*Assistant Examiner*—Tiffany A Fetzner

(57) ABSTRACT

The invention relates to a method for supporting an examination by means of an imaging diagnostic device. An examination mode is first selected by a user. At least one partial view of an examination object is subsequently generated and compared with a stored standard view, on which at least one accessory required for the examination mode is displayed. The comparison checks whether the at least one accessory is present on the partial view of the examination object. The result of the comparison is indicated to the user to ensure that the necessary accessories are present at a beginning of an actual examination even with a plurality of possible measuring methods.

9 Claims, 2 Drawing Sheets

METHOD FOR SUPPORTING AN MRI EXAMINATION BY MEANS OF POSITIONING AND CHECKING MRI ACCESSORY IMPLEMENTATION

CROSS REFERENCE TO RELATED APPLICATIONS

This application claims priority to the German Application No. 10 2005 013 851.9, filed Mar. 24, 2005 which is incorporated by reference herein in its entirety.

FIELD OF INVENTION

The present invention relates to a method for supporting an examination by means of an imaging diagnostic device.

BACKGROUND OF INVENTION

The use of imaging diagnostic devices, in particular computer tomographs or magnetic resonance devices, is expensive, which means that the optimum planning and implementation of an examination using such diagnostic devices is of vital importance. Magnetic resonance devices feature a number of measuring methods for examining a patient. In this case, different requirements must be fulfilled for several of the measuring methods. If a user of a magnetic resonance device forgets to install a high-frequency coil required for the subsequent examinations for instance, or it is incorrectly positioned, the examination process is unnecessarily delayed since the user must pull the patient back out of the magnetic resonance device in order to position the coils.

SUMMARY OF INVENTION

An object of the present invention is to specify a method for supporting an examination with the imaging diagnostic device, by means of which possible inadequacies during the implementation of the examination are recognized and can be easily eliminated.

This object is achieved by the claims. In this case, an examination mode is first selected by a user for instance. At least one partial view of an examination object is subsequently produced. The comparison of the at least one partial view with at least one stored standard view, on which at least one accessory required for the examination mode is displayed, checks whether the at least one accessory is present. The result of the comparison is displayed on a monitor for instance. This ensures that the necessary accessories are present at the beginning of the actual measurement even with a plurality of possible measuring methods and examinations. Accessories are understood here to include parts which must be attached to a patient by the user prior to the start of the examination for example, so as to support the examination and/or to actually to enable it.

In an advantageous embodiment of the invention, the imaging diagnostic device is a magnetic resonance device and a marker which can be detected by the magnetic resonance device is arranged on the accessory. This facilitates the detection of the accessory by the magnetic resonance device by means of a magnetic resonance measurement and likewise the comparison with the stored standard situation.

BRIEF DESCRIPTION OF THE DRAWINGS

Further advantages and features of the invention result from the subsequent description of an exemplary embodiment and with reference to the drawings, in which.

DETAILED DESCRIPTION OF INVENTION

Figure 1:
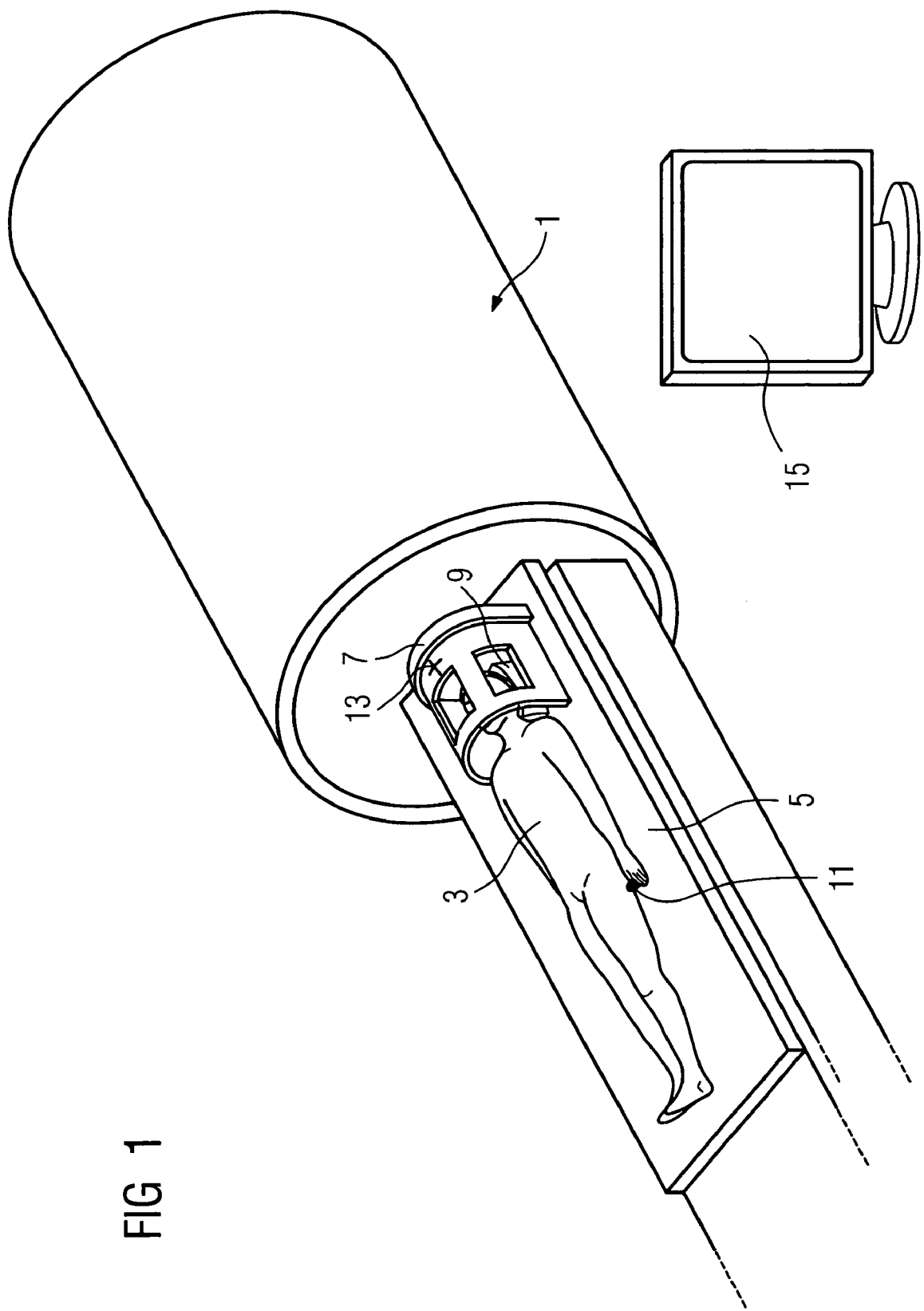
FIG. 1 shows a schematic magnetic resonance device and
FIG. 2 shows a schematic whole body view

In FIG. 1, a magnetic resonance device 1 and a patient 3 are displayed schematically. The patient 3 is positioned on a patient couch 5. A high frequency coil 7 is arranged at the head of the patient 3, said high frequency coil being used for a subsequent head examination. A patient pillow 9 is positioned under the head of the patient 3 in order to stabilize the head. Furthermore, an alarm ball 11 is located in the hand of the patient 3, by means of which the patient 3 can issue the operating personnel with an alarm signal during the examination. Markers are attached to the head coil 7 and also to the alarm ball 11 and the patient pillow 9, said markers being made of differently shaped reservoirs 13. Nevertheless, other markers which can be detected by means of the magnetic resonance measurements are essentially also possible. The markers on the alarm ball 11 and on the patient pillow 9 are not shown in FIG. 1 due to lack of space. They can be of a circular or rectangular design for instance. The reservoir 13 of the head coil 7 is shaped like a cross. In an alternative embodiment, the cross can be asymmetrically shaped, so as to be able to identify the orientation more easily. The respective reservoir 13 can be easily detected by the magnetic resonance device 1 within a magnetic resonance measurement and can be identified on the basis of the shape. The corresponding reservoirs are asymmetrically shaped in order to determine the orientation. This is not necessary with the alarm ball 11, as the orientation is irrelevant here.

After preparing for the measurement, in other words positioning the patient 3, connecting and fixing the head coil 7 and the patient pillow 9 as well as transferring the alarm ball 11, the patient 3 is moved into the magnetic resonance device 1. Before the actual examination is started, a whole body view of the patient 3 is recorded. Depending on the selected examination mode, the recording of only a partial body view is also possible. The markers of the positioned accessories, in other words the head coil 7, the alarm ball 11 and the patient pillow 9 can be recognized on the resulting image. On the basis of data entered by the operating personnel for the subsequent examination, by comparing the recorded whole body view with standard views stored in a database, which display a whole body view of another patient with correct positioning of the accessories required for the examination [lacuna]. This thus verifies whether all accessories required for the examination are present and whether they are in their correct position. The correct wiring of the head coil 7 is likewise verified.

If an accessory is not present or it is not correctly positioned, the operating personnel are issued with an alarm message on the monitor 15 of the magnetic resonance device 1. It is thus possible for things to be quickly remedied prior to the start of the actual examination. This is necessary for instance if the patient 3 has lost the alarm ball 11 or the patient pillow 9 is not attached in the correct position. If all accessories are present and correctly positioned, the measuring operation of the magnetic resonance device 1 is initiated, so that the actual examination can begin. During the examination, new whole body views of the patient 3 are recorded at regular intervals or if required and these are compared with the first whole body view or the stored standard views so as to check whether all accessories are furthermore correctly positioned. This ensures a rapid awareness of the situation in which a patient 3 loses the alarm ball 11 during the measurement for instance. If this is the case, a corresponding warning is displayed on the monitor 15 before the examination is continued.

If, at the start of the measurement, operating personnel inadvertently attached a chest coil or knee coil to the patient 3 instead of the head coil 9, this would be detected by comparing the recorded whole body view with the reference image and this could still be rectified before the start of the measurement. The comparison with the standard view can likewise determine whether the patient 3 is lying in a correct position on the patient couch.

Figure 2:
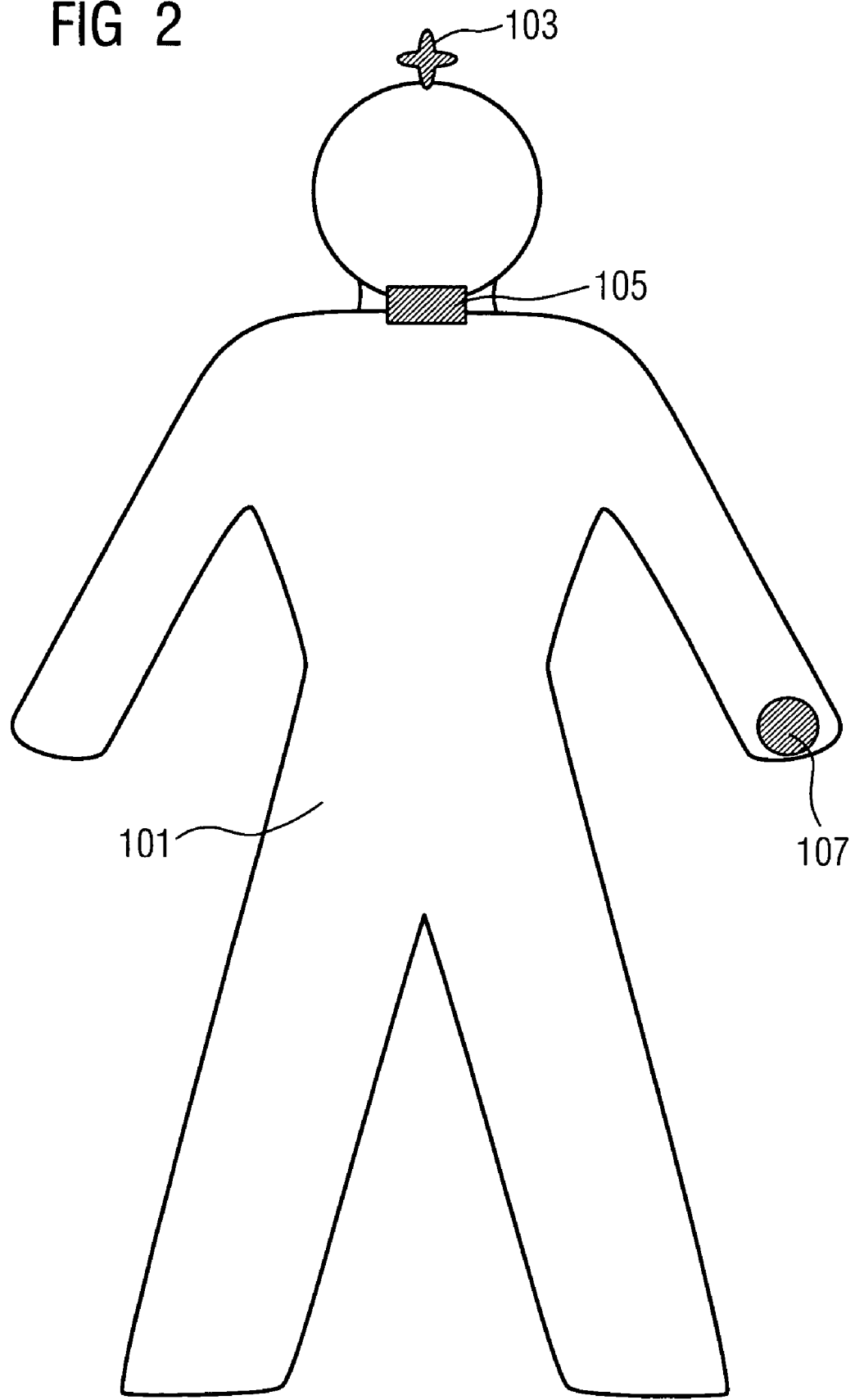

A whole body view 101 of the patient 3 is schematically displayed in FIG. 2. The markers of the head coil 103, the patient pillow 105 and the alarm ball 107 can be seen in the whole body view 101. The comparison with the standard view determines whether the position and orientation of the accessories correspond to the entered parameters of the measurement.

The whole body view is compared with the standard view by means of pattern recognition, in which the contour of the patient 3 is first matched to the contour of the body displayed in the standard view. The recorded markers are subsequently matched according to their shape by means of a pattern comparison. It is thus possible to determine whether they are present and attached in the correct position and orientation.

The method avoids the disadvantage occurring particularly during whole body examinations, where the patient 3 is practically completely covered with local coils, that the accessories, such as the alarm ball 11 and the patient pillow 9, arranged within the coils near to the patient 3 can be checked by the operating personal in terms of their position and presence by non-optical means. It is thus easily possible for the operating personal to forget to connect the coil or even to attach it.

Alternatively, a whole body view of the patient 3 is not required for special examinations. With a head examination for instance, a partial view of the patient 3 would also be sufficient to determine the correct positioning of accessories, said partial view displaying the head and torso regions. It is thus not possible to ensure whether coils have been inadvertently attached to the legs of the patient 3.

The invention claimed is:

1. A method for checking that all auxiliary MRI accessories (such as alarm balls, patient pillows, RF coils, etc.) are implemented (i.e. actively attached) and positioned correctly before initiating an MRI scan using a magnetic resonance device comprising:

initially positioning and actively implementing (i.e. actively attaching), all of the desired auxiliary MRI accessories about a patient that is to undergo the MRI scan, wherein all of the desired auxiliary MRI accessories have a separate identifiable marker, which is detectable by the MR device; and using the magnetic resonance device in order to test and check that all of the desired auxiliary MRI accessories are positioned and implemented correctly by generating an MRI test image having at least a partial view of the patient and which records on the generated test image the presence, position, and orientation of any detected auxiliary MRI accessory markers;

comparing, by means of pattern recognition, the generated test image showing the contour/shape of the patient and the position and orientation of each of the recorded markers for each of the detected auxiliary MRI accessories, which are active and implementation ready with a stored standard image showing all of the recorded auxiliary MRI accessory markers, when they are positioned/oriented correctly and are implementation ready (i.e. active, attached) in preparation for performing the MRI scan;

determining, via matched pattern comparison, that all of the auxiliary MRI accessories for performing the MRI scan are present, actively ready, and positioned/oriented correctly before initiating the MRI scan based on a result of the image comparison between the generated test image and the stored standard image; and displaying the result of the image comparison on a monitor, while issuing an alarm message when one or more of the auxiliary MRI accessories is not present, is absent, missing or is improperly positioned or is improperly oriented; and indicating readiness for the MRI scan, when all auxiliary MRI accessories are present and positioned/oriented properly based on the image comparison.

2. The method according to claim 1, wherein at least one of the auxiliary MRI accessories comprises an alarm ball for the patient, and the result of the comparison between the generated test image and the stored standard image is a position of the alarm ball with respect to the patient.

3. The method according to claim 1, wherein at least one of the auxiliary MRI accessories comprises a patient pillow and the result of the comparison between the generated test image and the stored standard image is a position of the patient pillow with respect to the patient.

4. The method according to claim 1, wherein each marker which is detectable by the magnetic resonance device is arranged on one or more auxiliary MRI accessories such that each of said markers is made of a differently shaped reservoir.

5. The method according to claim 4, wherein at least one of the auxiliary MRI accessories comprises a high-frequency coil.

6. The method according to claim 1, further comprising:
generating a further test image having at least a further partial view of the patient using the magnetic resonance device; and
comparing the further test image with the stored standard image showing the auxiliary MRI accessories.

7. The method according to claim 6, further comprising: comparing the further test image to the test image.

8. The method according to claim 1, further comprising: generating a plurality of further test images, each further test image having at least a further partial view of the patient using the magnetic resonance device; and comparing each further test image with the stored standard image showing all of the auxiliary MRI accessories.

9. The method according to claim 1, wherein the partial view is replaced by a full-bodied view of the patient.

* * * * *